(12) United States Patent
Grönberg

(10) Patent No.: US 9,743,931 B2
(45) Date of Patent: Aug. 29, 2017

(54) DEVICE AND A METHOD FOR ANASTOMOSIS

(71) Applicant: CARPONOVUM AB, Halmstad (SE)

(72) Inventor: Anders Grönberg, Halmstad (SE)

(73) Assignee: CARPONOVUM AB, Halmstad (SE)

( * ) Notice: Subject to any disclaimer, the term of this patent is extended or adjusted under 35 U.S.C. 154(b) by 155 days.

(21) Appl. No.: 14/421,254

(22) PCT Filed: Aug. 16, 2013

(86) PCT No.: PCT/SE2013/050979
§ 371 (c)(1),
(2) Date: Feb. 12, 2015

(87) PCT Pub. No.: WO2014/031065
PCT Pub. Date: Feb. 27, 2014

(65) Prior Publication Data
US 2015/0201942 A1    Jul. 23, 2015

(30) Foreign Application Priority Data
Aug. 20, 2012   (SE) ..................................... 1250933

(51) Int. Cl.
*A61B 17/08*    (2006.01)
*A61B 17/11*    (2006.01)
*A61B 17/064*   (2006.01)

(52) U.S. Cl.
CPC ............ *A61B 17/11* (2013.01); *A61B 17/1114* (2013.01); *A61B 17/0643* (2013.01); *A61B 2017/1132* (2013.01)

(58) Field of Classification Search
CPC ............ A61B 17/11; A61B 2017/1103; A61B 2017/1107; A61B 2017/111; A61B 17/1114; A61B 2017/1132; A61B 17/0643
See application file for complete search history.

(56) References Cited

U.S. PATENT DOCUMENTS 5,346,501 A *  9/1994  Regula ................ A61B 17/1114
                                                    606/151
6,517,556 B1 *  2/2003  Monassevitch ..... A61B 17/1114
                                                    606/151
(Continued)

FOREIGN PATENT DOCUMENTS

DE          19542733 A1    7/1997
EP           1908420 A1    4/2008
(Continued)

*Primary Examiner* — Jonathan Miles
(74) *Attorney, Agent, or Firm* — Capitol City TechLaw

(57) ABSTRACT

A device (100) for arrangement on the side wall of an intestine is provided. The device (100) comprises a first member (10) and a second member (20) of a generally hollow open configuration. The first member (10) comprises an elastic part (11), with a first and a second axial end, and a rigid support part (12), arranged at the first axial end of the elastic part (11). The second member (20) comprises a first and a second axial end, said first end of the second member (20) matching the shape of the second axial end of the elastic part (11), such that an intestine wall may be uniformly distributed between the second axial end of the elastic part (11) and the second member (20). The device (100) also comprises a connection member (30) for connecting the rigid support part (12) and the second member (20) to each other. A method for arranging said device at the side wall of a tubular structure, and a connector (200) for connecting two devices (100) is also provided.

13 Claims, 5 Drawing Sheets

(56) References Cited

U.S. PATENT DOCUMENTS

| | | | | |
|---|---|---|---|---|
| 6,569,173 | B1* | 5/2003 | Blatter | A61B 17/0643 606/153 |
| 6,884,250 | B2* | 4/2005 | Monassevitch | A61B 17/1114 606/151 |
| 2001/0004697 | A1* | 6/2001 | Blatter | A61B 17/0643 606/153 |
| 2001/0029383 | A1* | 10/2001 | Solem | A61B 17/0643 606/153 |
| 2002/0049459 | A1* | 4/2002 | Kato | A61B 17/11 606/153 |
| 2003/0040761 | A1* | 2/2003 | Pugsley | A61B 17/0643 606/151 |
| 2004/0116945 | A1* | 6/2004 | Sharkawy | A61B 17/0643 606/153 |
| 2009/0105734 | A1* | 4/2009 | Gronberg | A61B 17/1114 606/153 |
| 2009/0138030 | A1* | 5/2009 | Gronberg | A61B 17/11 606/153 |
| 2011/0098732 | A1* | 4/2011 | Jacobs | A61B 17/0643 606/153 |
| 2012/0323234 | A1* | 12/2012 | Weisshaupt | A61B 17/0643 606/33 |
| 2013/0304100 | A1* | 11/2013 | Gronberg | A61B 17/1114 606/153 |

FOREIGN PATENT DOCUMENTS

| | | | |
|---|---|---|---|
| EP | 2380507 | A1 | 10/2011 |
| WO | 2007122220 | A2 | 11/2007 |
| WO | 2007122223 | A1 | 11/2007 |

\* cited by examiner

DEVICE AND A METHOD FOR ANASTOMOSIS

This application claims priority under 35 USC 119(a)-(d) to SE patent application No. 1250933-7, which was filed on Aug. 20, 2012, the entire content of which is incorporated herein by reference.

TECHNICAL FIELD

The present invention relates to anastomosis of a living tissue, and more particularly to a device for compression anastomosis of tubular structures. Furthermore, the invention relates to a method for mounting the device to a tubular structure.

BACKGROUND OF THE INVENTION

Colorectal cancer is the third most frequent type of cancer in the world having an occurrence of about 1 million new cases every year. The incidents of cancer are considerably more frequent in the industrial part of the world.

Current techniques for mechanically performing anastomosis of hollow organs use circular mechanical staplers, which execute the connection of the tissue edges of the dissected hollow organ by metallic or plastic staples. A wide variety of surgical staplers have been developed for gastric, oesophageal and intestinal surgery. In performing surgical anastomotic stapling, generally two pieces of the hollow organ are joined by a ring of staples with a closed loopstapler. End to end anastomoses are generally performed by intraluminal surgical staplers that deliver a pair of staggered rings of staples. During this process, a circular knife blade is used to separate the tissue that is held within the circular ring. The separated tissue is then removed with the stapler to form a circular opening within the lumen along the stapling line.

A major issue regarding anastomosis healing is the blood circulation of the anastomosis during the healing process. Despite substantial development of surgical techniques during the last decades, morbidity and mortality after resections in the gastrointestinal tract, e.g. due to anastomotic leakage, remain as serious problems. Ischemia and inflammation, which are natural parts of the healing process, may cause leakage and secondary infection that may be fatal for the patient in the stapling area. Therefore, it has become common practice to relieve the pressure from the anastomosis by performing a deviating stoma, especially when the anastomosis is carried out in the lower part of colon and in rectum. By relieving pressure and faecal stream from the anastomosis during the healing process, the leakage incident may be reduced and fatal consequences of anastomotic dehiscence can be avoided. The inconvenience for the patient is obvious, since the patient must have a temporary stoma for a time period of about 3 to 6 months, and then has to undergo a second surgery in order to close the stoma. Unfortunately in many cases, the closure of the stoma cannot be reversed and the patient is forced to live with a permanent stoma leading to lower quality of life associated with increased costs.

Additionally, there is an increased risk of anastomotic stenosis, surgical staplers create a smaller and more rigid opening compared to the cross section of the original lumen due to the staples inside the hollow structure connecting the two ends thereof, i.e. a collar may be formed that may lead to stenosis.

Hence, there has been a need in the technical field to develop assemblies overcoming these disadvantages. One such assembly is disclosed in WO 2007122223, wherein an assembly comprising interlocking members for use in achieving anastomosis of tubular organs is disclosed. The assembly comprises two rigid parts, onto which two elastic rings are arranged, to secure intestine ends, respectively, in between each rigid part and corresponding elastic part, whereafter the rigid parts are interconnected via a connection member. It is however difficult to use such open end anastomotic rings for connecting the side of an intestine to another side or an open end, which is often called for due to tumours with difficult access.

SUMMARY OF THE INVENTION

Accordingly, the present invention preferably seeks to mitigate, alleviate or eliminate one or more of the above-identified deficiencies in the art and disadvantages singly or in any combination and solves at least the above mentioned problems by providing a device for arrangement on the side wall of an intestine, said device comprising a first member and a second member of a generally hollow open configuration, wherein the first member comprises an elastic part, with a first and a second axial end, and a rigid support part, arranged at the first axial end of the elastic part, wherein the second member comprises a first and a second axial end, said first end of the second member matching the shape of the second axial end of the elastic part, such that an intestine wall may be uniformly distributed between the second axial end of the elastic part and the second member, and a connection member for connecting the rigid support part and the second member to each other.

For the same reasons a method for mounting the device according to above to a tubular structure, comprising the steps of: incising the wall of the tubular structure; arranging the first member of a generally hollow open configuration in the lumen of the tubular structure, such that the second axial end thereof is in contact with the inner wall of the tubular structure and said first member further being positioned around the incision created during the incising of the wall of the tubular structure; connecting said first member and said second member to each other, such that the wall of the tubular structure is arranged in between the elastic part and the second member; and cutting the wall of the tubular structure along the inner edge of the first and second member.

A connector for connecting two devices according to above to each other is also provided to realize versatile connection at difficult intestinal areas, said connector having a generally hollow open configuration, and said connector comprising: slits extending axially from the free ends thereof around the periphery forming tongues between the slits; and a tubular part arranged centrally of the slits and tongues on the free ends of the connector, wherein the tubular part is provided with at least one hole for connection to a catheter.

Further objects, features and advantages of the present invention will appear from the following detailed description, from the attached drawings as well as from the dependent claims.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DESCRIPTION OF EMBODIMENTS

In FIGS. 1 to 7, a device 100 for connection to the side wall of an intestine is disclosed. This device 100 may then in turn be connected to another such device 100, connected to the side wall of another part of this intestine, or it may be connected to another anastomotic device, said other anastomotic device comprising a first member comprising a rigid part and a elastic part, and a connection member, wherein the connection member may be integrated with the rigid part of the other anastomotic device or it may be a separate connection member, that may be snap fitted into cooperation with both the device 100 according to FIG. 1 and the rigid part of the other anastomotic device. The device 100 for arrangement on the side wall of an intestine comprises a first member 10 and a second member 20. The first member 10 and the second member 20 are both of a generally hollow open configuration.

Figure 2:
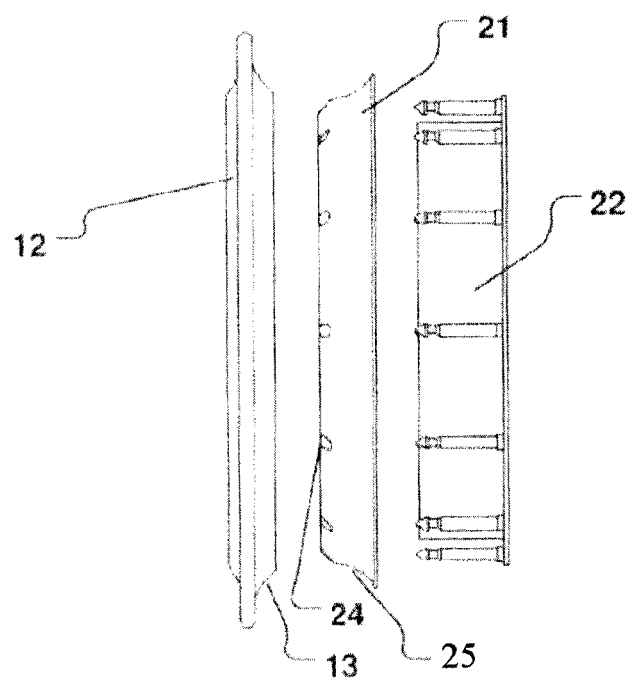
FIG. 2 is a side and exploded view of an anastomotic device according to one embodiment of the present invention.
Figure 3:
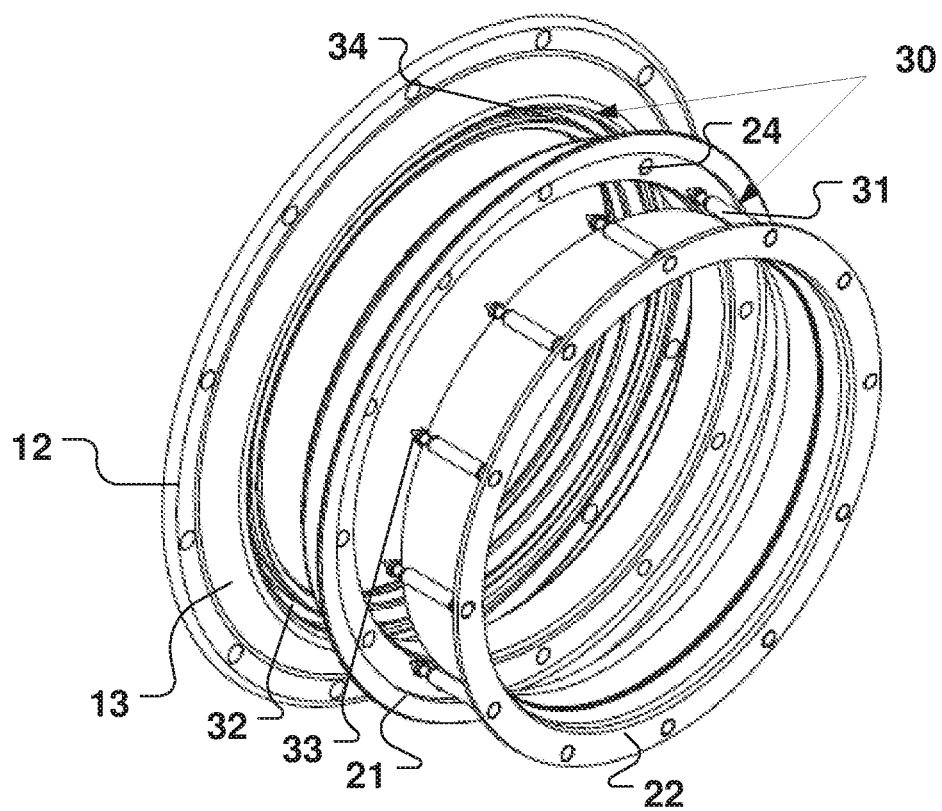
FIG. 3 is a perspective and exploded view of an anastomotic device according to one embodiment of the present invention, without an elastic part for easier illustration of the other parts.

The first member 10 comprises an elastic part 11 and a rigid support part 12, which is disclosed in FIGS. 2 and 3 (wherein the elastic part 11 has been omitted for clearer view of the other parts). The elastic part 11 is a substantial circular symmetric ring and is made as a compact body or as a tube, which may be filled with air, gas or fluid, and are made of an elastic polymeric material of for example 40 to 70 Shore. The rigid support part 12 may be of a polymeric material, more specifically a biocompatible material and most specifically a biodegradable material, of a rigidity adequate to stabilize the elastic part 11. The elastic part 11 may for example be an elastic ring of a suitable polymeric or rubber material, such as an elastomer. The elastic part 11 may also be biocompatible and/or biodegradable. The elastic part may have a ring shaped cross-section. The elastic part 11 has a first and a second axial end. The rigid support part 12 is arranged at the first axial end of the elastic part 11. The rigid support part 12 is also ring shaped, with one side thereof adapted to receive the elastic part 11. This side of the rigid support part 12 may then have an elastic part seat 13. The elastic part seat 13 may be concavely shaped to receive the convex axial end of the elastic part 11. The elastic part 11 may be attached to the rigid support part 12 through glueing or through over-moulding or co-moulding.

During removal of a tumour from an intestine, the affected part of the intestine is removed by cutting the intestine on a suitable distance on each side of the intestine. Depending on where and how the tumour was located, there may be a need to connect the side of one of the free ends of the intestine with a side of the other free end of the intestine, or there may be a need to connect the side of one free end with the other free end. The device according to FIGS. 1 and 2 allows for creating a connection through the side of one such free end.

When connecting the side of a free end of an intestine, the open end is first closed with sutures. Then the intestine is incised at a suitable position. Thereafter, the first member 10 is inserted through the incision, and is placed in the lumen of the intestine, such that the second axial end thereof is in contact with the inner wall of the intestine and said first member 10 further being positioned around the incision created during the incising of the wall of the tubular structure. After positioning the first member 10 within the intestine, the incision may be decreased in size with sutures, to facilitate arrangement of the first member 10 around the incision.

After positioning the first member 10 within the lumen of the intestine, the second member 20 is positioned correspondingly on the outside of the intestine. The second member 20 comprises a first and a second axial end. The first end of the second member 20 matches the shape of the second axial end of the elastic part 11, such that an intestine wall may be uniformly distributed between the second axial end of the elastic part 11 and the second member 20. For connecting the first 10 member 10 to the second member 20 a connection member 30 is provided. The connection member 30 may be at least one male part 31 on the second member and at least one female part 32 on the first member 10. In the embodiment disclosed in FIGS. 1, 2, and 3, the male parts 31 on the second member 20 are pins 31, and the rigid support part 12 on the first member 10 comprises corresponding female parts 32 in form of holes or slits 32, such that the second part 20 may be brought into connection with the first part 10 by inserting the pins 31 into the holes or slits 32. The pins 31 on the second part 20 may comprise barbs 33 and the holes or slits 32 on the rigid support part 12 on the first member 10 may have flanges 34 at their mouths, to interlock the first part 10 to the second part 20 at a suitable distance from each other, at which the pressure on the intestine squeezed between the elastic part 11 of the first member 10 and the second member 20.

Figure 1:
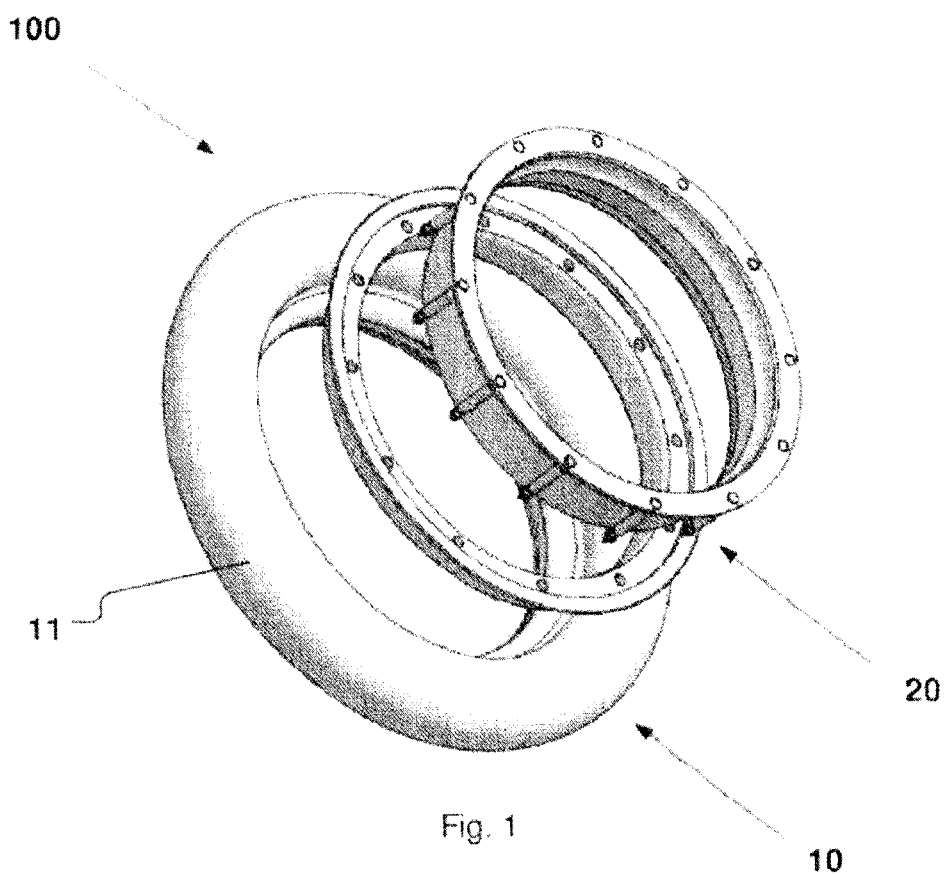
FIG. 1 is a perspective and exploded view of an anastomotic device according to one embodiment of the present invention.

The second member 20, according to the embodiment in FIGS. 1, 2, and 3, comprises an intestine interacting part 21 and a pin carrying part 22. The intestine interacting part 21 and a pin carrying part 22 are preferably made of a polymeric material, more specifically a biocompatible material and most specifically a biodegradable material. The pins 31 extending from the pin carrying part 22 are preferably of a biocompatible metallic material, but rigid polymers are also envisioned. The intestine interacting part 21 has a concave intestine/elastic part seat 25 at its first axial end, intended to face the intestine and the first member 10, such that the round shape of the elastic part 11, shaping the intestine in contact therewith, may sit on the second member 20 in a convenient way. The intestine interacting part 21 has holes or slits 24 and said pin carrying part 22 is provided with the pins 31. The pins 31 are received in the holes or slits 24, such that the pins are accessible to interact with the support part 12 of the first member 10. In this way manufacturing of the second member 20 is facilitated, since it may be difficult to arrange pins on the concave surface of the intestine interacting part 21 while simultaneously arranging said pins to correspond in position and direction to the holes or slits 32 on the rigid support part 12 on the first member 10.

Figure 4:
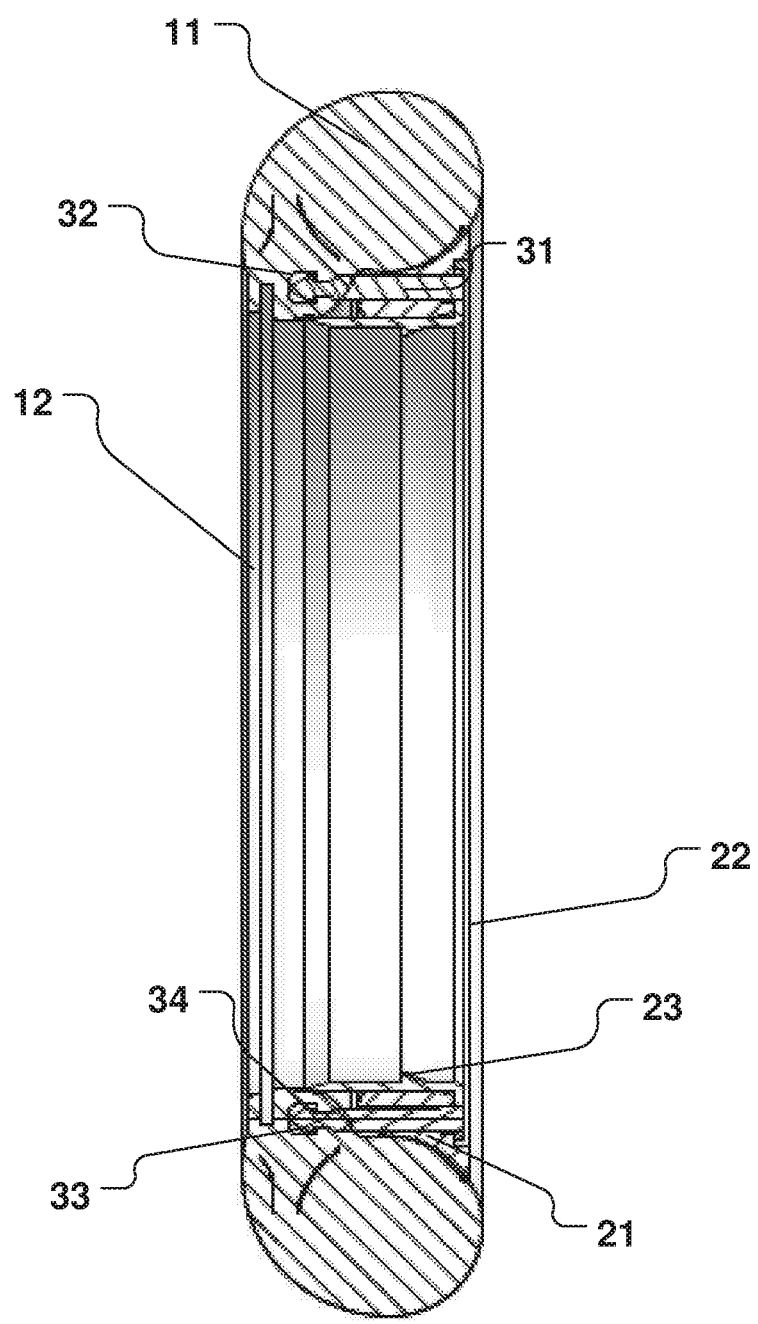
FIG. 4 is a cross sectional view of an anastomotic device according to one embodiment of the present invention.
Figure 5:
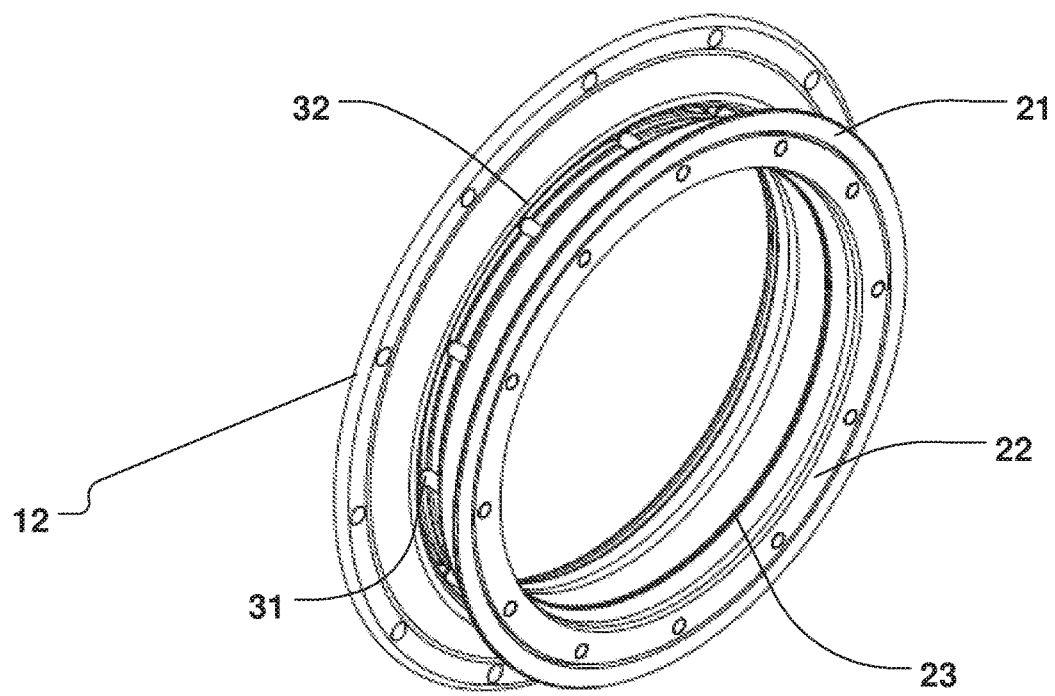
FIG. 5 is a perspective view of an anastomotic device according to one embodiment of the present invention, without an elastic part for easier illustration of the other parts.
Figure 6:
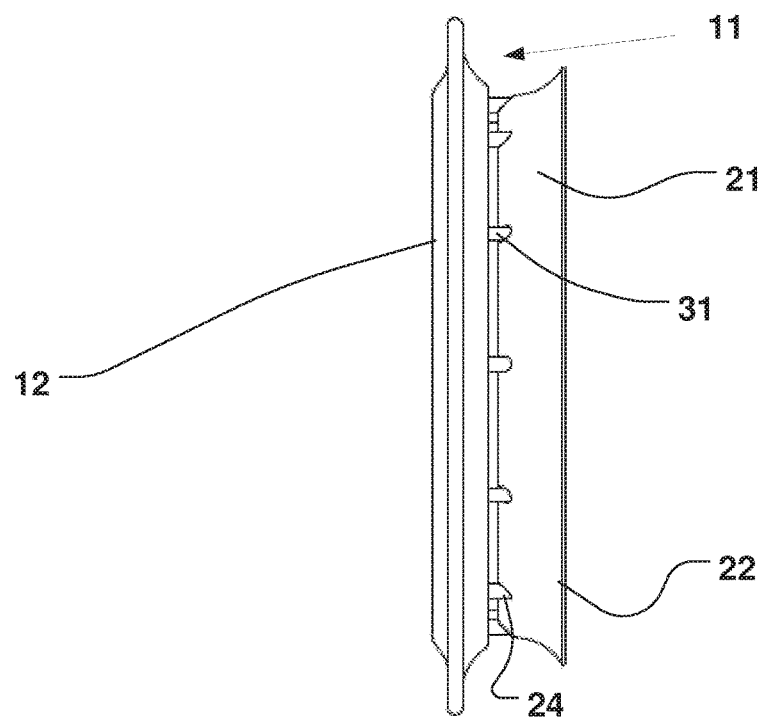
FIG. 6 is a side view of an anastomotic device according to one embodiment of the present invention, without an elastic part for easier illustration of the other parts.

When bringing the first member 10 and the second member 20 together, as disclosed in FIGS. 4 to 6 (in FIGS. 5 and 6 the elastic part 11 has been omitted for clearer view of the other parts), the pins 31 will penetrate the wall of the intestine around the incision, whereafter they will enter the holes or slits 32 on the rigid support part 12 on the first member 10. Then the barbs 33 and the flanges 34 will interact to interlock the first member 10 to the second member 20. In this way the first member 10 and the second member 20 are connected to each other, radially inwards of the elastic part 11, and the intestine wall is squeezed at a uniform pressure between the elastic part 11 of the first member 10 and the concave intestine/elastic part seat 25.

Thereafter, the superfluous intestine tissue around the incision within the edges of the first member 10 and the second member 20 may be cut along the inner edges of the first member 10 and the second member 20.

The second member 20 may be provided with a ridge 23 on its inner surface, for allowing the device 100 to be attached to another device 100 or another anastomotic device, of the kind referred to above, and as disclosed in WO2007122223. Such other anastomotic device may thus comprise a first member comprising a first rigid part and a second elastic part and a connection member. The rigid part and the elastic part have a generally hollow open configuration. The connection member may be integral with the first rigid part.

Figure 7:
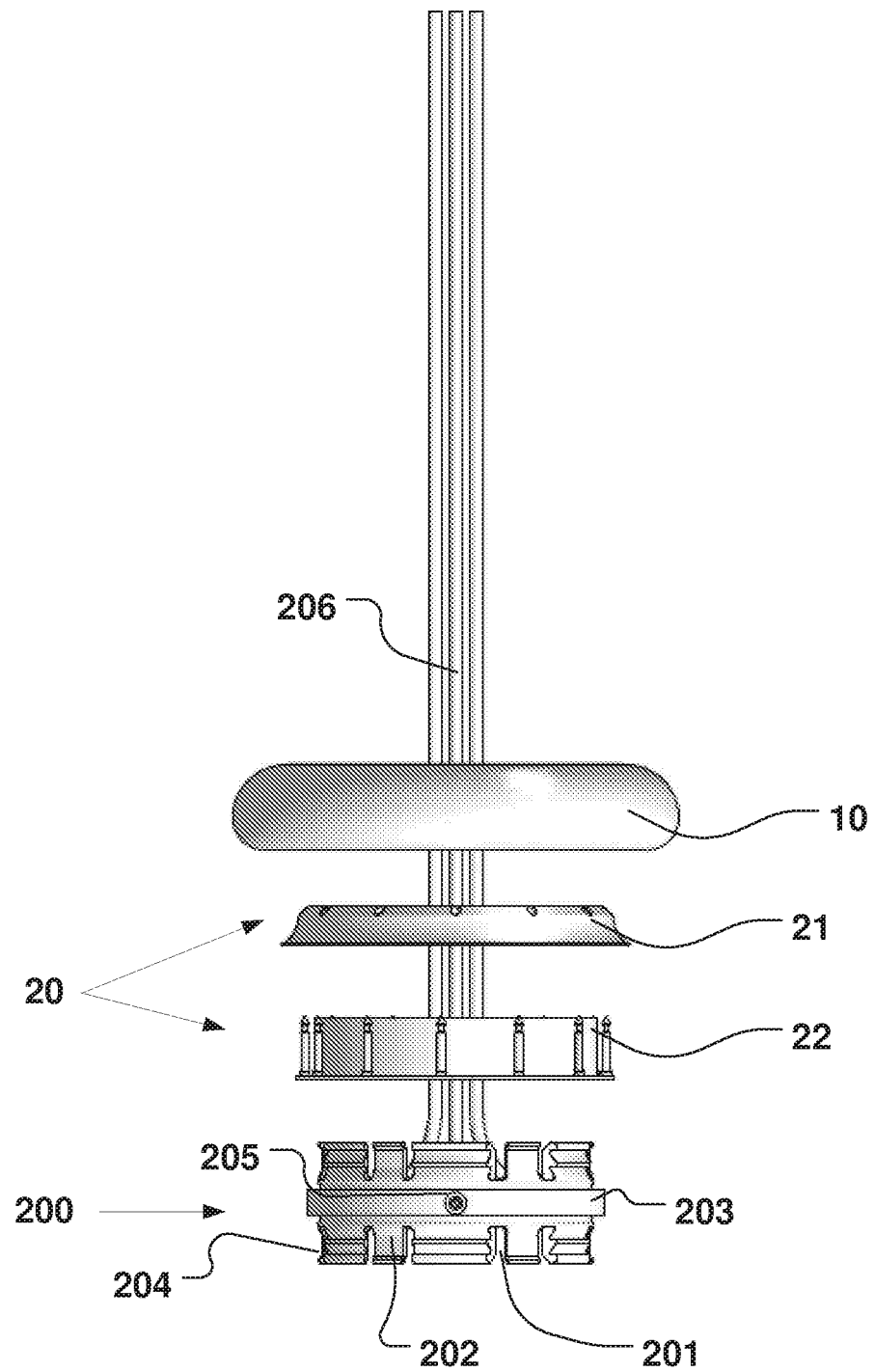
FIG. 7 is a side and exploded view of an anastomotic device according to one embodiment of the present invention, together with an embodiment of a connector.

Alternatively, a separate connector 200, disclosed in FIG. 7 together with the device 100, may be used to connect two devices 100, and thus two sides of a cut intestine. The separate connector 200 may naturally also be used to connect the device 100 to the anastomotic device according to the prior art WO2007122223.

The separate connector 200 has a generally hollow open configuration. The separate connector 200 is provided slits 201 extending axially from the free ends thereof around the periphery forming tongues 202 between the slits 201. Centrally of the slits 201 and tongues 202 a central tubular part 203 is arranged. At least one of the tongues 202 on each side is provided with an outward protrusion 204 arranged adjacent or at a distance from the free ends of the tongues 202. The number of slits 201 may vary, and the length of the slits 201 can be as long as half the width of the connection member 200. The slits 201 may however be shorter, as long as they under the circumstances may be adequately compressed to snap fit the protrusion 204 beyond, i.e. centrally of, the ridge 23 of the second member 20. The slits 201 are either symmetrical or unsymmetrical provided around the periphery, forming tongues 202 with a similar or varying width. The number of tongues 202 can vary, for example 2 to 10 may be provided, which can be arranged symmetrical or unsymmetrical around the periphery. The central tubular part 203 may be provided with through holes 205 that may be connected to catheters 206. The catheters 206 have a length allowing for following the intestine out through the anus of the patient, such that air or water may be pushed through the catheters to check the sealing pressure between the elastic parts 11, with accommodated intestine walls there between.

Herein above, several embodiments of the invention are described with reference to the drawings in order to enable a skilled person to perform the invention. However, the features and method steps included in these embodiments do not limit the invention. Moreover, the features and method steps may be combined in other manners than specifically described.

The cross sections of the elastic parts 11 are shown as substantially circular. However, other shapes may be used, such as rectangular, triangular, hexagonal, octagonal, etc. The outer surface of the rigid parts 12, 21 comprises a recess intended to receive the elastic parts 11 respectively. This recess has a shape that is at least partly complementary to the shape of the elastic part 11. Thus, the recess may be rectangular, triangular, hexagonal, octagonal, etc.

The configuration or outer shapes of the elastic parts 11 are shown to be substantially cylindrical having a circular outer contour. However, other shapes are possible, such as rectangular, triangular, hexagonal, octagonal etc.

The elastic parts can be only partially elastic. The elasticity is used for squeezing the tubular structure between the elastic parts 11 and the rigid parts 12, 21, respectively, with a certain force. Other means performing the same function is possible to use.

In an alternate embodiment, the top cone may be snapped onto the central axle, as well as the end-hat of the handle. Furthermore, the truncated cone can be made as a whole piece, which can be released from the axle through rectum at low anastomoses.

In the claims, the term "comprises/comprising" does not exclude the presence of other elements or steps. Furthermore, although individually listed, a plurality of means, elements or method steps may be implemented. Additionally, although individual features may be included in different embodiments, these may possibly be combined in other ways, and the inclusion in different embodiments does not imply that a combination of features is not feasible. In addition, singular references do not exclude a plurality. The terms "a", "an" does not preclude a plurality. Reference signs in the claims are provided merely as a clarifying example and shall not be construed as limiting the scope of the claims in any way.

The invention claimed is:

1. A device for arrangement on an intestine wall, the device comprising:
   a first member having a hollow open configuration and a second member having a hollow open configuration,
   wherein the first member includes
      an elastic part, with a first axial end and a second axial end, and
      a rigid support part, arranged at the first axial end of the elastic part;
   wherein the second member includes a first axial end and a second axial end, the first axial end of the second member matching the shape of the second axial end of the elastic part, such that the intestine wall may be uniformly distributed between the second axial end of the elastic part and the second member; and
   a connection member for connecting the rigid support part and the second member to each other;
   wherein the connection member includes pins on the second member and a pin receiver on the rigid support part;
   wherein the pins extend in an axial direction toward the rigid support part; and
   wherein the pins are radially inward of the elastic part.

2. The device according to claim 1, wherein the elastic part has a circular cross section, such that the first and the second axial ends thereof are convexly rounded; and
   wherein the first axial end of the second member has a part that is concavely shaped to match the convexly rounded second axial end of the elastic part.

3. The device according to claim 1, wherein the pins have distal ends provided with barbs.

4. The device according to claim 1, wherein the pin receiver on the rigid support part comprises holes or a slit, having at least one mouth in the direction towards the second axial end of the elastic part, the at least one mouth being able to receive the pins in a retaining manner.

5. The device according to claim 4, wherein the mouth edge of the at least one mouth is resilient.

6. The device according to claim 1, wherein the second member comprises an intestine interacting part and a pin carrying part, the intestine interacting part having holes or slits and the pin carrying part having the pins, such that the holes or slits may receive the pins there through, such that the pins are accessible to interact with the rigid support part of the first member.

7. The device according to claim 1, wherein the first and the second members are ring shaped.

8. The device according to claim 1, wherein the elastic part is made of a polymeric material.

9. The device according to claim 1, wherein the elastic part is made of a biocompatible material.

10. The device according to claim 1, wherein the elastic part is made of a biodegradable material.

11. The device according to claim 1, wherein the second member has a ridge on its inner surface.

12. A method for mounting the device according to claim 1 to a tubular structure, the method comprising:
    incising the wall of the tubular structure;
    arranging the first member in the lumen of the tubular structure, such that the second axial end of the first member is in contact with the inner wall of the tubular structure, and such that the first member is positioned around the incision created during the incising of the wall of the tubular structure;
    connecting the first member and the second member to each other, such that the wall of the tubular structure is arranged between the elastic part and the second member; and
    cutting the wall of the tubular structure along the inner edge of the first and the second member.

13. The method according to claim 12, wherein the pressure is essentially uniform on the wall of the tubular structure between the elastic part and the second member.

* * * * *